United States Patent
Nakashima et al.

(10) Patent No.: US 11,924,712 B2
(45) Date of Patent: Mar. 5, 2024

(54) INFORMATION PROCESSING APPARATUS, NON-TRANSITORY COMPUTER READABLE MEDIUM, AND INFORMATION PROCESSING METHOD

(71) Applicant: TOYOTA JIDOSHA KABUSHIKI KAISHA, Aichi-ken (JP)

(72) Inventors: Toyokazu Nakashima, Nagoya (JP); Shunsuke Sagara, Nisshin (JP); Naoya Oka, Nagakute (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 232 days.

(21) Appl. No.: 17/457,876

(22) Filed: Dec. 6, 2021

(65) Prior Publication Data

US 2022/0182789 A1     Jun. 9, 2022

(30) Foreign Application Priority Data

Dec. 7, 2020     (JP) .................................. 2020-203029

(51) Int. Cl.
   *H04W 4/029*     (2018.01)
   *G16H 40/67*     (2018.01)

(52) U.S. Cl.
   CPC ............ *H04W 4/029* (2018.02); *G16H 40/67* (2018.01)

(58) Field of Classification Search
   CPC .............................. H04W 4/029; G16H 40/67
   USPC ........................................................ 455/456.1
   See application file for complete search history.

(56) References Cited

U.S. PATENT DOCUMENTS

| | | | |
|---|---|---|---|
| 2014/0207806 A1* | 7/2014 | Sharma | G06F 16/9038 707/755 |
| 2019/0357031 A1* | 11/2019 | Wickham | H04W 4/90 |
| 2022/0028544 A1* | 1/2022 | Elmaleh | G06Q 20/102 |

FOREIGN PATENT DOCUMENTS

JP               201645916 A       4/2016

\* cited by examiner

*Primary Examiner* — Qutbuddin Ghulamali
(74) *Attorney, Agent, or Firm* — HAUPTMAN HAM, LLP

(57) ABSTRACT

An information processing apparatus includes a controller configured to generate a message notifying a healthcare professional of information on a call concerning a patient, and associate, when the healthcare professional takes out an AED while going to the patient based on the message, the call with information on an installation location from which the AED is taken out.

14 Claims, 5 Drawing Sheets

INFORMATION PROCESSING APPARATUS, NON-TRANSITORY COMPUTER READABLE MEDIUM, AND INFORMATION PROCESSING METHOD

CROSS-REFERENCE TO RELATED APPLICATION

This application claims priority to Japanese Patent Application No. 2020-203029, filed on Dec. 7, 2020, the entire contents of which are incorporated herein by reference.

TECHNICAL FIELD

The present disclosure relates to an information processing apparatus, a program, and an information processing method.

BACKGROUND

Automated External Defibrillators (AEDs) are becoming increasingly popular and have been installed in many locations.

Patent literature (PTL) 1 discloses a parking lot management system in which an AED storage box is installed in a parking lot payment machine.

CITATION LIST

Patent Literature

PTL 1: JP 2016-45916 A

SUMMARY

When an AED is taken out for treatment, it may be difficult to know where the AED has been taken if it is carried far from the location of installation.

It would be helpful to enable identification of where an AED has been taken.

An information processing apparatus according to the present disclosure includes a controller configured to:
  generate a message notifying a healthcare professional of information on a call concerning a patient; and
  associate, when the healthcare professional takes out an AED while going to the patient based on the message, the call with information on an installation location from which the AED is taken out.

A program according to the present disclosure is configured to cause a computer to execute operations including:
  generating a message notifying a healthcare professional of information on a call concerning a patient; and
  associating, when the healthcare professional takes out an AED while going to the patient based on the message, the call with information on an installation location from which the AED is taken out.

An information processing method according to the present disclosure includes:
  generating a message notifying a healthcare professional of information on a call concerning a patient; and
  associating, when the healthcare professional takes out an AED while going to the patient based on the message, the call with information on an installation location from which the AED is taken out.

The present disclosure enables the identification of where an AED has been taken.

DETAILED DESCRIPTION

An embodiment of the present disclosure is described below with reference to the drawings.

Figure 1:
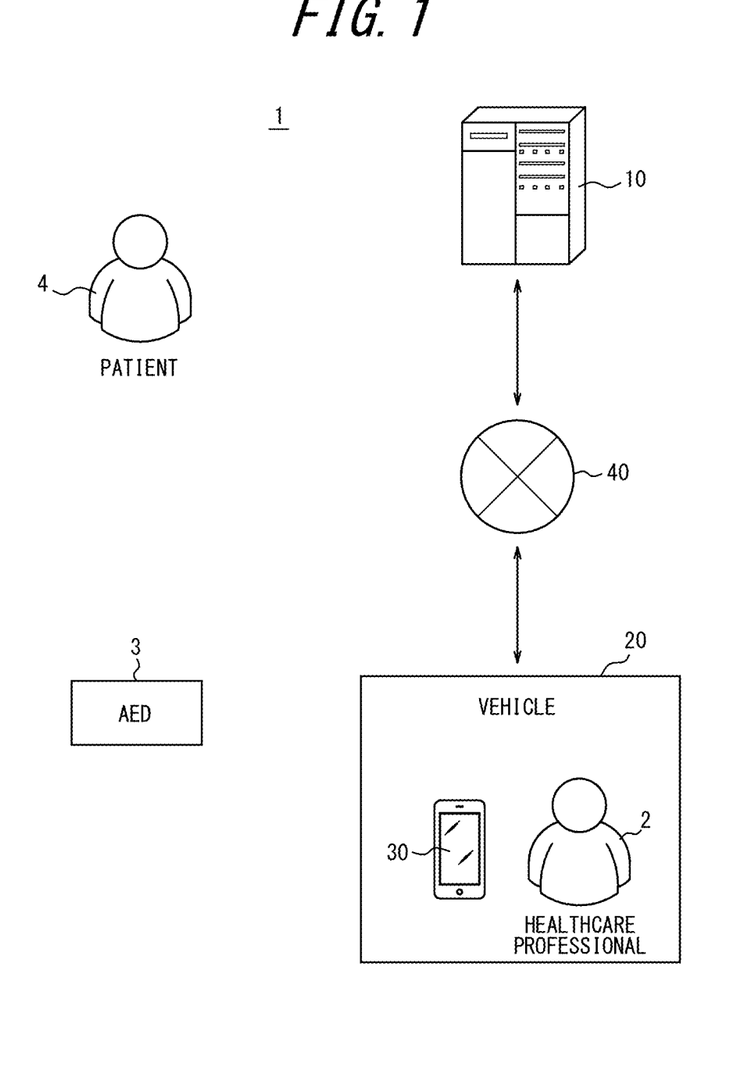
FIG. 1 is a diagram illustrating a configuration of an information processing system according to an embodiment of the present disclosure.

FIG. 1 is a diagram illustrating a configuration of an information processing system 1 according to an embodiment of the present disclosure. The configuration and outline of the information processing system 1 according to an embodiment of the present disclosure are described with reference to FIG. 1.

The information processing system 1 includes an information processing apparatus 10, a vehicle 20, and a terminal apparatus 30. The information processing apparatus 10, the vehicle 20, and the terminal apparatus 30 are communicably connected via a network 40. The network 40 may be a network including a mobile communication network, the Internet, and the like.

In FIG. 1, one each of the information processing apparatus 10, the vehicle 20, and the terminal apparatus 30 are illustrated, but the number of information processing apparatuses 10, vehicles 20, and terminal apparatuses 30 may be two or more of each.

As illustrated in FIG. 1, the vehicle 20 is a vehicle with a healthcare professional 2 on board. The terminal apparatus 30 is a terminal apparatus owned by the healthcare professional 2 who is on board the vehicle 20.

The healthcare professional 2 may be a doctor, nurse, paramedic, or the like.

An AED 3 is an AED installed in a predetermined location. The healthcare professional 2 can take out the AED 3 when necessary for treatment. Although FIG. 1 illustrates one AED 3, a plurality of AEDs 3 may be installed at their respective predetermined locations.

A patient 4 is a patient in a non-hospital setting such as a home or the street. The patient 4 calls an organization capable of dealing with emergency patients, such as an emergency center, to indicate that treatment is needed. In the present embodiment, the case of the organization that can respond to emergency patients being an emergency center is described as an example. The patient 4 need not be the one who calls the emergency center. For example, a third party who notices something wrong with the patient 4 may call the emergency center.

The information processing apparatus 10 is, for example, a dedicated computer configured to function as a server. The information processing apparatus 10 may be a general purpose personal computer (PC).

The information processing apparatus 10 can communicate with the vehicle 20 and the terminal apparatus 30 via the network 40. Upon acquiring information on the call concerning the patient 4 from the emergency center or the like, the information processing apparatus 10 generates a message notifying the healthcare professional 2 of the information on the call concerning the patient 4 and transmits the message to the terminal apparatus 30 of the healthcare professional 2 or to the vehicle 20 that has the healthcare professional 2 on board. The "message notifying the healthcare professional 2 of the information on the call concerning the patient 4" is also referred to below simply as a "message".

When the healthcare professional 2 who saw the message takes out the AED 3 before going to the patient 4 based on the message, the information processing apparatus 10 stores information on the installation location from which the AED 3 was taken out in association with the call.

The vehicle 20 can communicate with the information processing apparatus 10 and the terminal apparatus 30 via the network 40. The vehicle 20 may be any type of automobile, such as a gasoline-powered vehicle, a diesel-powered vehicle, an HEV (Hybrid Electric Vehicle), a PHEV (Plug-in Hybrid Electric Vehicle), a BEV (Battery Electric Vehicle), a FCEV (Fuel Cell Electric Vehicle), or the like. Driving of the vehicle 20 may be automated at any level. The automation level is, for example, any one of Level 1 to Level 5 according to the level classification defined by the Society of Automotive Engineers (SAE). The vehicle 20 may be a dedicated Mobility as a Service (MaaS) vehicle.

The terminal apparatus 30 can communicate with the information processing apparatus 10 and the vehicle 20 via the network 40. The terminal apparatus 30 may, for example, be a smartphone or a tablet.

Figure 2:
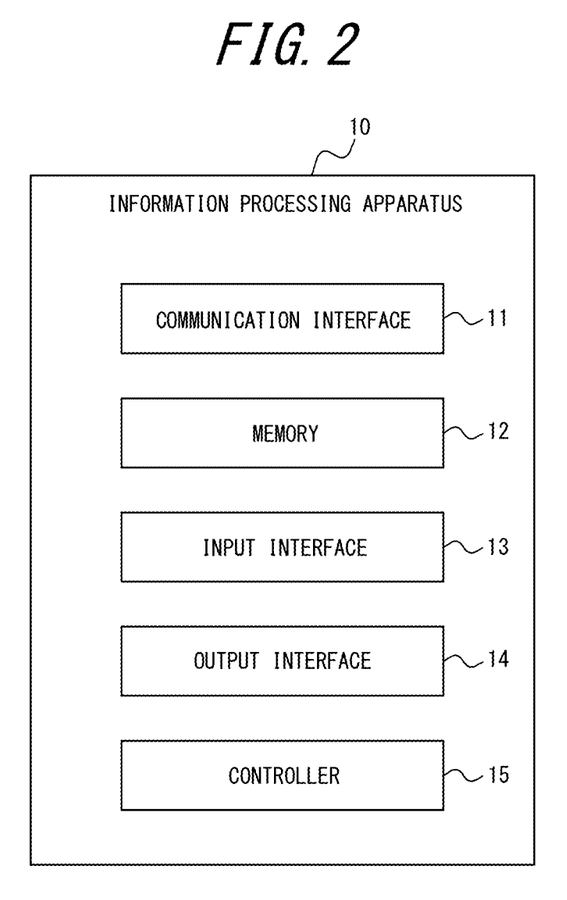
FIG. 2 is a block diagram illustrating a configuration of an information processing apparatus according to an embodiment of the present disclosure.

A configuration of the information processing apparatus 10 according to an embodiment of the present disclosure is described with reference to FIG. 2.

The information processing apparatus 10 includes a communication interface 11, a memory 12, an input interface 13, an output interface 14, and a controller 15.

The communication interface 11 includes a communication module connected to the network 40. For example, the communication interface 11 may include a communication module corresponding to a local area network (LAN). In an embodiment, the information processing apparatus 10 is connected to the network 40 via the communication interface 11. The communication interface 11 transmits and receives various information via the network 40. The communication interface 11 can communicate with the vehicle 20 and the terminal apparatus 30 via the network 40.

The memory 12 is, for example, a semiconductor memory, a magnetic memory, an optical memory, or the like, but is not limited to these. The memory 12 may function as, for example, a main memory, an auxiliary memory, or a cache memory. The memory 12 stores any information used in operations of the information processing apparatus 10. For example, the memory 12 may store a system program, an application program, various types of information received by the communication interface 11, and the like. The information stored in the memory 12 may be updated with information received from the network 40 via the communication interface 11, for example. A portion of the memory 12 may be installed externally to the information processing apparatus 10. In this case, the externally installed portion of the memory 12 may be connected to the information processing apparatus 10 via any appropriate interface.

The input interface 13 includes one or more input interfaces for detecting user input and acquiring input information based on user operation. For example, the input interface 13 includes, but is not limited to, a physical key, a capacitive key, a touchscreen integrally provided with a display of the output interface 14, or a microphone that receives audio input.

The output interface 14 includes one or more output interfaces for outputting information to notify the user. For example, the output interface 14 includes, but is not limited to, a display for outputting information as images, a speaker for outputting information as audio, or the like.

The controller 15 includes at least one processor, at least one dedicated circuit, or a combination thereof. The processor is a general purpose processor, such as a central processing unit (CPU) or a graphics processing unit (GPU), or a dedicated processor specialized for particular processing. The dedicated circuit is, for example, a field-programmable gate array (FPGA) or an application specific integrated circuit (ASIC). The controller 15 executes processes related to operations of the information processing apparatus 10 while controlling components of the information processing apparatus 10.

Figure 3:
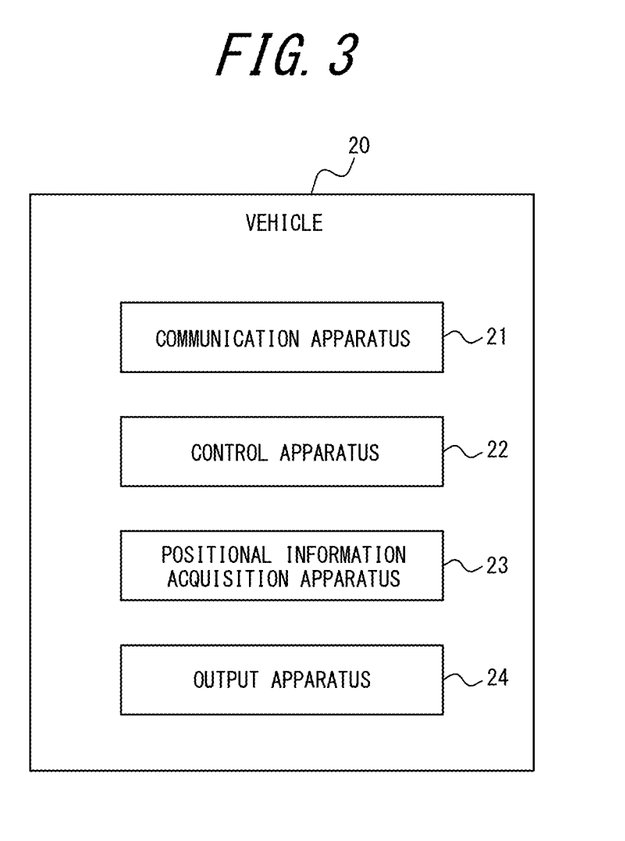
FIG. 3 is a block diagram illustrating a configuration of a vehicle according to an embodiment of the present disclosure.

A configuration of the vehicle 20 according to an embodiment of the present disclosure is described with reference to FIG. 3.

The vehicle 20 includes a communication apparatus 21, a control apparatus 22, a positional information acquisition apparatus 23, and an output apparatus 24. The communication apparatus 21, the control apparatus 22, the positional information acquisition apparatus 23, and the output apparatus 24 are communicably connected via an in-vehicle network, such as Controller Area Network (CAN), or dedicated lines, for example.

The communication apparatus 21 includes a communication module that connects to the network 40. For example, the communication apparatus 21 may include a communication module compliant with mobile communication standards such as long term evolution (LTE) and the 4th generation (4G) and the 5th generation (5G) standards. In an embodiment, the vehicle 20 is connected to the network 40 via the communication apparatus 21. The communication apparatus 21 transmits and receives various information via the network 40. The communication apparatus 21 can communicate with the information processing apparatus 10 and the terminal apparatus 30 via the network 40.

The control apparatus 22 includes at least one processor, at least one dedicated circuit, or a combination thereof. The processor is a general purpose processor such as a CPU or a GPU, or a dedicated processor that is dedicated to specific processing. The dedicated circuit is, for example, an FPGA or an ASIC. The control apparatus 22 executes processing related to the operation of the vehicle 20 while controlling each component of the vehicle 20.

The positional information acquisition apparatus 23 includes at least one receiver compliant with a satellite positioning system. For example, the positional information acquisition apparatus 23 may include a global positioning system (GPS) receiver. The positional information acquisition apparatus 23 acquires the measured value of the position of the vehicle 20 as the positional information. The positional information includes, for example, an address, a latitude, a longitude, an altitude, and the like.

The output apparatus 24 includes one or more output interfaces for outputting information to notify the user. For example, the output apparatus 24 includes, but is not limited to, a display for outputting information as video, a speaker for outputting information as audio, or the like.

Figure 4:
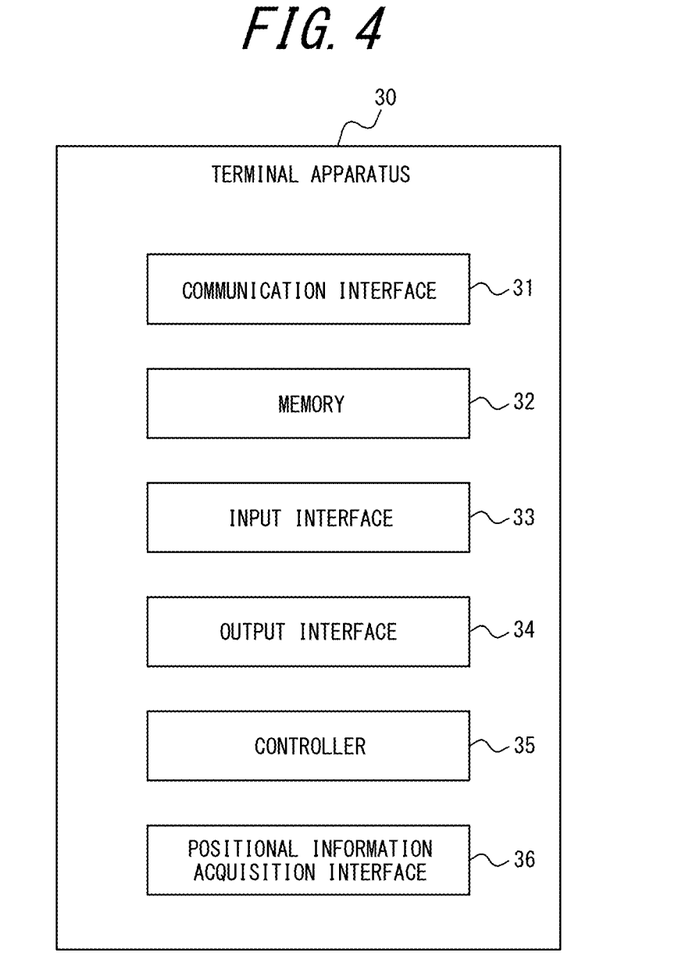
FIG. 4 is a block diagram illustrating a configuration of a terminal apparatus according to the embodiment of the present disclosure.

A configuration of the terminal apparatus 30 according to an embodiment of the present disclosure is described with reference to FIG. 4.

The terminal apparatus 30 includes a communication interface 31, a memory 32, an input interface 33, an output interface 34, a controller 35, and a positional information acquisition interface 36.

The communication interface 31 includes a communication module connected to the network 40. For example, the communication interface 31 may include a communication module compliant with mobile communication standards such as LTE, 4G and 5G. In an embodiment, the terminal apparatus 30 is connected to the network 40 via the communication interface 31. The communication interface 31 transmits and receives various information via the network 40. The communication interface 31 can communicate with the information processing apparatus 10 and the vehicle 20 via the network 40.

The memory 32 is, for example, a semiconductor memory, a magnetic memory, an optical memory, or the like, but is not limited to these. The memory 32 may function as, for example, a main memory, an auxiliary memory, or a cache memory. The memory 32 stores any information used in operations of the terminal apparatus 30. For example, the memory 32 may store a system program, an application program, various types of information received by the communication interface 31, and the like. The information stored in the memory 32 may be updated with information received from the network 40 via the communication interface 31, for example. A portion of the memory 32 may be installed externally to the terminal apparatus 30. In this case, the externally installed portion of the memory 32 may be connected to the terminal apparatus 30 via any appropriate interface.

The input interface 33 includes one or more input interfaces for detecting user input and acquiring input information based on user operation. The input interface 33 is, for example, a physical key, a capacitive key, a touchscreen integrally provided with a display of the output interface 34, a microphone for receiving audio input, or the like, but is not limited to these.

The output interface 34 includes one or more output interfaces for outputting information to notify the user. For example, the output interface 34 includes, but is not limited to, a display for outputting information as images, a speaker for outputting information as audio, or the like.

The controller 35 includes at least one processor, at least one dedicated circuit, or a combination thereof. The processor is a general purpose processor such as a CPU or a GPU, or a dedicated processor that is dedicated to specific processing. The dedicated circuit is, for example, an FPGA or an ASIC. The controller 35 executes processes related to operations of the terminal apparatus 30 while controlling components of the terminal apparatus 30.

The positional information acquisition interface 36 includes at least one receiver compliant with a satellite positioning system. For example, the positional information acquisition interface 36 may include a GPS receiver. The positional information acquisition interface 36 acquires a measured value of the position of the terminal apparatus 30 as positional information. The positional information includes, for example, an address, a latitude, a longitude, an altitude, and the like.

(Operations of Information Processing System)

Operations of the information processing system 1 illustrated in FIG. 1 are described with reference to FIGS. 1 to 4.

The patient 4 is a patient in need of treatment in a non-hospital setting, such as at home or on the street. The patient 4 or a third party who notices something wrong with the patient 4 notifies the emergency center that the patient 4 needs treatment.

An information and communication device, such as a server installed in an emergency center, transmits the information on the call concerning the patient 4 to the information processing apparatus 10. The information on the call concerning the patient 4 may, for example, include the name of the patient, the date and time the call was received, the position of the patient, the condition of the patient, whether an AED is required, etc. The "information on the call concerning the patient 4" is also referred to below simply as "call information".

The communication interface 11 of the information processing apparatus 10 receives the call information transmitted by the information communication device installed in the emergency center. The controller 15 acquires the call information, transmitted by the information and communication device installed in the emergency center, via the communication interface 11.

The memory 12 stores positional information for a plurality of healthcare professionals 2. The healthcare professionals 2 whose positional information is stored by the memory 12 are healthcare professionals who have consented to register their positional information.

The memory 12 stores, in association with the healthcare professional 2, information such as identification information for the terminal apparatus 30 owned by the healthcare professional 2, positional information for the terminal apparatus 30, identification information for the vehicle 20 owned by the healthcare professional 2, and positional information for the vehicle 20.

Here, the positional information for the healthcare professional 2 may be positional information for the terminal apparatus 30 owned by the healthcare professional 2. When the healthcare professional 2 is on board the vehicle 20, the position of the terminal apparatus 30 of the healthcare professional 2 matches the position of the vehicle 20 of the healthcare professional 2. Here, the position of the terminal apparatus 30 of the healthcare professional 2 matching the position of the vehicle 20 of the healthcare professional 2 is not limited to the case of the positions completely matching, but rather includes the case of the position of the terminal apparatus 30 of the healthcare professional 2 being within a predetermined distance from the position of the vehicle 20 of the healthcare professional 2.

The positional information, stored by the memory 12, for the terminal apparatus 30 of the healthcare professional 2 is periodically updated. The positional information for the terminal apparatus 30 of the healthcare professional 2 is periodically updated by the information processing apparatus 10 periodically acquiring the positional information for the terminal apparatus 30. The controller 35 of the terminal apparatus 30 periodically transmits the positional information for the terminal apparatus 30 acquired by the positional information acquisition interface 36 to the information processing apparatus 10 via the communication interface 31.

The positional information for the vehicle 20 of the healthcare professional 2 stored by the memory 12 is periodically updated. The positional information for the vehicle 20 of the healthcare professional 2 is periodically updated by the information processing apparatus 10 periodically acquiring the positional information for the vehicle 20. The control apparatus 22 of the vehicle 20 periodically transmits the positional information for the vehicle 20 acquired by the positional information acquisition apparatus 23 to the information processing apparatus 10 via the communication apparatus 21.

Upon acquiring the call information, the controller 15 generates a message to notify the healthcare professional 2 of the call information. The controller 15 refers to the memory 12 and extracts the information on a healthcare professional 2 who is at a position close to the position of the patient 4. At this time, the controller 15 may extract information on a healthcare professional 2 who is at a position close to the position of the patient 4 based on the positional information for the terminal apparatus 30 of the healthcare professional 2.

The controller 15 transmits the generated message via the communication interface 11 to the healthcare professional 2 who is closest to the position of the patient 4. The controller 15 may transmit the message to the terminal apparatus 30 of the healthcare professional 2 via the communication interface 11. Alternatively, when the position of the terminal apparatus 30 of the healthcare professional 2 who is closest to the position of the patient 4 matches the position of the vehicle 20, and the healthcare professional 2 is therefore inferred to be on board the vehicle 20, the message may be transmitted to the vehicle 20 of the healthcare professional 2 via the communication interface 11. It is assumed below that the controller 15 transmits the message to the terminal apparatus 30 of the healthcare professional 2 via the communication interface 11.

The communication interface 31 of the terminal apparatus 30 receives the message transmitted by the information processing apparatus 10. The controller 35 acquires the message transmitted by the information processing apparatus 10 via the communication interface 31.

The controller 35 causes the output interface 34 to output the message. The message outputted by the output interface 34 includes information on the call concerning the patient 4. The controller 35 may cause the output interface 34 to display the message as an image or to output the message as audio.

The input interface 33 accepts input from the healthcare professional 2 regarding the message. The input from the healthcare professional 2 includes information on whether the healthcare professional 2 is able to go to the patient 4.

The controller 35 transmits the information accepted from the healthcare professional 2 by the input interface 33 to the information processing apparatus 10 via the communication interface 31.

The communication interface 11 of the information processing apparatus 10 receives, from the terminal apparatus 30, the input from the healthcare professional 2 regarding the message. The controller 15 acquires the input from the healthcare professional 2 regarding the message via the communication interface 11.

When the input acquired from the terminal apparatus 30 includes information indicating an inability to go to the patient 4, the controller 15 transmits a message via the communication interface 11 to the terminal apparatus 30 of the healthcare professional 2 who is at the next closest position to the position of the patient 4. The controller 15 repeats the process of transmitting a message via the communication interface 11 to the terminal apparatus 30 of the healthcare professional 2 until information indicating an ability to go to the patient 4 is acquired from the terminal apparatus 30. At this time, the controller 15 may transmit messages to the terminal apparatus 30 of the healthcare professional 2 while prioritizing the messages in order of proximity to the position of the patient 4.

The healthcare professional 2 who has provided input to the input interface 33 of the terminal apparatus 30 indicating the ability to go to the patient 4 then goes to the patient 4. If the healthcare professional 2 is on board the vehicle 20, the healthcare professional 2 may ride in the vehicle 20 to the patient 4. If the vehicle 20 is capable of automatic driving, the vehicle 20 may automatically drive to the patient 4. The vehicle 20 may, in this case, acquire the positional information for the patient 4 from the information processing apparatus 10 and set the destination to the position of the patient 4.

The message that the controller 35 of the terminal apparatus 30 acquires from the information processing apparatus 10 includes information on whether an AED is required. When the output interface 34 outputs information indicating that an AED is required, the healthcare professional 2 goes to the location where the AED 3 is installed, takes out the AED 3, and then goes to the patient 4 to provide first aid to the patient 4.

When the AED 3 is taken out, the healthcare professional 2 inputs information on the installation location from which the AED 3 was taken out to the input interface 33 of the terminal apparatus 30. The controller 35 transmits the information on the installation location of the AED 3 to the information processing apparatus 10 via the communication interface 31.

The communication interface 11 of the information processing apparatus 10 receives information on the installation location of the AED 3. The controller 15 acquires information on the installation location of the AED 3 via the communication interface 11.

The controller 15 stores the information on the installation location of the AED 3 in the memory 12 in association with the information on the call concerning the patient 4.

The call information stored in the memory 12 is thereby associated with the information on the installation location from which the AED 3 was taken out for the patient 4 of the call information. Therefore, by accessing the call information stored in the memory 12, it is possible to know to which installation location the AED 3 was taken out from for which call.

For example, when a staff member of the hospital into which the patient 4 has been transported wants to return the AED 3 used for treatment of the patient 4 to the original location where the AED 3 was installed, the staff member of the hospital can acquire information on the installation location of the AED 3 by accessing the call information stored in the memory 12 of the information processing apparatus 10. At this time, the staff member of the hospital may, for example, input the name of the patient and search for the installation location of the AED 3.

For example, when an administrator of the installation location of the AED 3 notices that the AED 3 has been taken out and wants to know where the AED 3 was taken, the administrator of the AED 3 can access the call information stored in the memory 12 of the information processing apparatus 10 to acquire information on which call the AED 3 was used for. At this time, the administrator of the AED 3 may, for example, input the installation location of the AED 3 and search for the call with which the AED 3 is associated.

<Inference of Installation Location of AED that was Taken Out>.

In the above embodiment, the case of a healthcare professional 2 inputting, to the terminal apparatus 30, information on the installation location of the AED 3 that was taken out is described, but when the healthcare professional 2 boards the vehicle 20 and goes to the patient 4, the information processing apparatus 10 may infer the installation location of the AED 3 that was taken out based on the positional information for the vehicle 20.

When the controller 15 of the information processing apparatus 10 acquires information from the terminal apparatus 30 of the healthcare professional 2 indicating the ability to go to the patient 4, the controller 15 acquires the positional information for the terminal apparatus 30 of the healthcare professional 2 and the positional information for the vehicle 20 of the healthcare professional 2, which are stored in the memory 12.

When the position of the terminal apparatus 30 of the healthcare professional 2 matches the positional information for the vehicle 20 of the healthcare professional 2, the controller 15 judges that the healthcare professional 2 is on board the vehicle 20. The controller 15 periodically acquires, via the communication interface 11, the positional information for the vehicle 20 from the vehicle 20 that has the healthcare professional 2 on board.

The memory 12 stores information on the installation locations of the plurality of AEDs 3.

When the controller 15 judges that the vehicle 20, which has on board the healthcare professional 2 who is going to the patient 4, stopped for a predetermined time or longer at any installation location among the installation locations, stored in the memory 12, of a plurality of AEDs 3, the controller 15 infers that the AED 3 was taken out from that installation location.

The controller 15 stores information on the inferred installation location of the AED 3 in the memory 12 in association with the information on the call concerning the patient 4.

Figure 5:
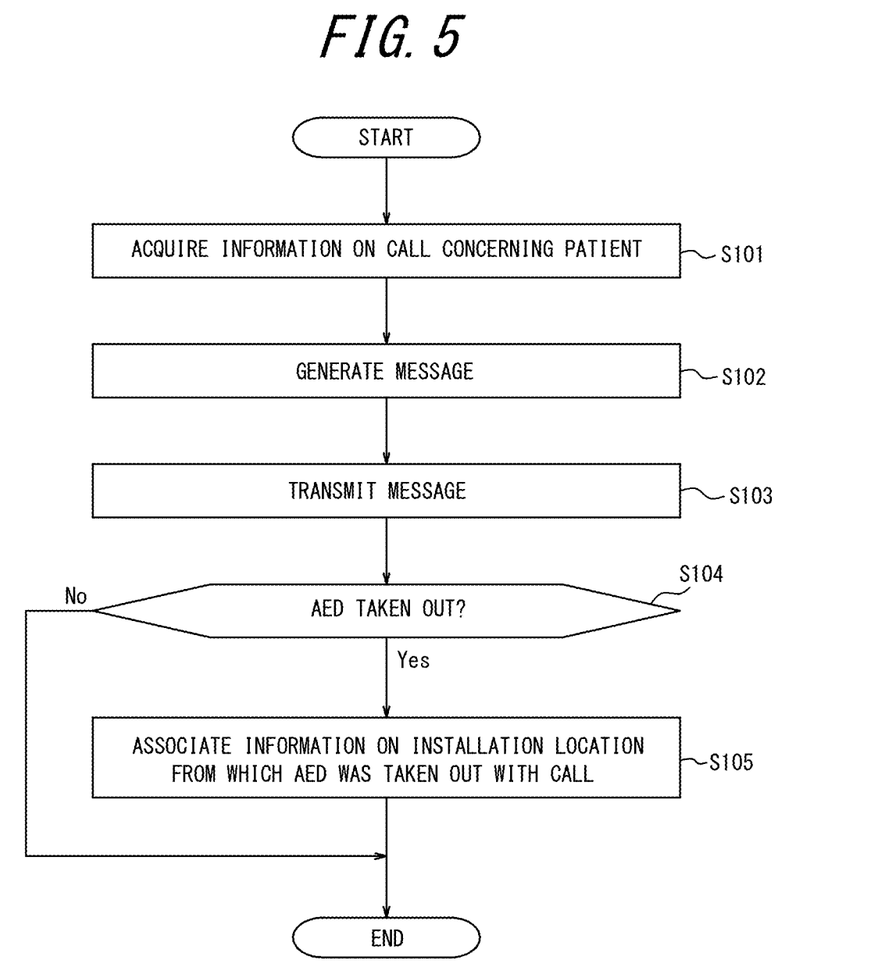
FIG. 5 is a flowchart illustrating operations of an information processing system according to an embodiment of the present disclosure.

Operations of the information processing system 1 are described with reference to the flowchart in FIG. 5.

In step S101, the controller 15 of the information processing apparatus 10 acquires, via the communication interface 11, information on a call concerning the patient 4, the information being transmitted by the information communication device installed in the emergency center.

In step S102, the controller 15 generates a message to notify the healthcare professional 2 of the call information.

In step S103, the controller 15 transmits a message via the communication interface 11 to the healthcare professional 2 who is closest to the position of the patient 4.

In step S104, the controller 15 judges whether an AED 3 was taken out from any of the installation locations. The controller 15 judges that the AED 3 was taken out when the healthcare professional 2 inputs the installation location of the AED 3 to the terminal apparatus 30 and the controller 15 acquires information on the installation location of the AED 3 from the terminal apparatus 30 via the communication interface 11. Alternatively, when the controller 15 judges that the vehicle 20, which has on board the healthcare professional 2 who is going to the patient 4, stopped for a predetermined period of time or longer at any of the installation locations of a plurality of AEDs 3, the controller 15 infers that the AED 3 was taken out from that installation location.

When it is judged that the AED 3 was not taken out (step S104: No), the controller 15 ends the process.

When it is judged that the AED 3 was taken out (step S104: Yes), the controller 15 advances to step S105.

In step S105, the controller 15 stores the information on the installation location of the AED 3 taken out by the healthcare professional 2 in the memory 12 in association with the information on the call concerning the patient 4.

As described above, in the information processing apparatus 10 of the present embodiment, the controller 15 generates a message notifying the healthcare professional 2 of the information on the call concerning the patient 4, and when the healthcare professional 2 who goes to the patient 4 based on the message takes out the AED 3, the information on the installation location where the AED 3 was taken out is associated with the call. In this way, since information on the installation location of the AED 3 that was taken out is associated with the call, it is possible to identify which call the AED 3 was taken out in response to. By referring to the information on the call, it is possible to identify which patient the AED 3 was used on. The information processing apparatus 10 according to the present embodiment can therefore identify where the AED 3 was taken.

The present disclosure is not limited to the embodiment described above. For example, a plurality of blocks described in the block diagrams may be integrated, or a block may be divided. Instead of executing a plurality of steps described in the flowcharts in chronological order in accordance with the description, the plurality of steps may be executed in parallel or in a different order according to the processing capability of the apparatus that executes each step, or as required. Other modifications can be made without departing from the spirit of the present disclosure.

For example, some of the processing operations executed in the information processing apparatus 10 in the above embodiment may be executed in the vehicle 20 or the terminal apparatus 30.

For example, some of the processing operations executed in the terminal apparatus 30 in the above embodiment may be executed in the vehicle 20.

For example, a configuration that causes a general purpose electronic device such as a smartphone, a computer, or the like to function as the information processing apparatus 10 according to the embodiment described above is possible. Specifically, a program in which processes for realizing the functions of the information processing apparatus 10 or the like according to the embodiment are written may be stored in a memory of the electronic device, and the program may be read and executed by a processor of the electronic device. Accordingly, in an embodiment, the present disclosure can also be implemented as a program executable by a processor.

In the above embodiment, the case of the healthcare professional 2 boarding the vehicle 20 of the healthcare professional 2 to go to the patient 4 has been described, but the vehicle 20 that the healthcare professional 2 boards is not limited to the vehicle 20 owned by the healthcare professional 2. For example, a third party other than the healthcare professional 2 may let the healthcare professional 2 board a vehicle 20 owned by the third party and then go to the patient 4.

In the above embodiment, the case of the healthcare professional 2 taking out the AED 3 and going to the patient 4 has been described, but a third party other than the healthcare professional 2 may carry the AED 3 to the patient 4. In this case, the healthcare professional 2 may go to the patient 4 without carrying the AED 3.

In the above embodiment, the healthcare professional 2 is described as going to the patient 4, but the person going to the patient 4 is not limited to the healthcare professional 2. For example, a member of the public who has taken a course in first aid may go to the patient 4.

The invention claimed is:

1. An information processing apparatus comprising a controller configured to:
   generate a message notifying a healthcare professional of information on a call concerning a patient; and
   associate, when the healthcare professional takes out an AED while going to the patient based on the message, the call with information on an installation location from which the AED is taken out, wherein
   when a position of a terminal apparatus of the healthcare professional matches a position of a vehicle of the healthcare professional, the controller is configured to judge that the healthcare professional is on board the vehicle, and
   upon judging that the vehicle has stopped for a predetermined time or longer at any installation location among installation locations of a plurality of AEDs, the controller is configured to infer that the AED has been taken out from the installation location.

2. The information processing apparatus of claim 1, wherein the controller is configured to transmit the message to the terminal apparatus or the vehicle.

3. The information processing apparatus of claim 1, further comprising a memory configured to store positional information for a plurality of healthcare professionals.

4. The information processing apparatus of claim 3, wherein the controller is configured to transmit the message to the healthcare professional whose positional information is close to a position of the patient.

5. The information processing apparatus of claim 3, wherein the memory is configured to store information on installation locations of a plurality of AEDs.

6. A non-transitory computer readable medium storing a program configured to cause a computer to execute operations comprising:
   generating a message notifying a healthcare professional of information on a call concerning a patient;
   associating, when the healthcare professional takes out an AED while going to the patient based on the message, the call with information on an installation location from which the AED is taken out;
   judging, when a position of a terminal apparatus of the healthcare professional matches a position of a vehicle of the healthcare professional, that the healthcare professional is on board the vehicle; and
   inferring, when it is judged that the vehicle has stopped for a predetermined time or longer at any installation location among installation locations of a plurality of AEDs, that the AED has been taken out from the installation location.

7. The non-transitory computer readable medium of claim 6, wherein the operations further comprise transmitting the message to the terminal apparatus or the vehicle.

8. The non-transitory computer readable medium of claim 6, wherein the operations further comprise storing positional information for a plurality of healthcare professionals.

9. The non-transitory computer readable medium of claim 8, wherein the operations further comprise transmitting the message to the healthcare professional whose positional information is close to a position of the patient.

10. The non-transitory computer readable medium of claim 6, wherein the operations further comprise storing information on installation locations of a plurality of AEDs.

11. An information processing method comprising:
    generating a message notifying a healthcare professional of information on a call concerning a patient;
    associating, when the healthcare professional takes out an AED while going to the patient based on the message, the call with information on an installation location from which the AED is taken out;
    judging, when a position of a terminal apparatus of the healthcare professional matches a position of a vehicle of the healthcare professional, that the healthcare professional is on board the vehicle; and
    inferring, when it is judged that the vehicle has stopped for a predetermined time or longer at any installation location among installation locations of a plurality of AEDs, that the AED has been taken out from the installation location.

12. The information processing method of claim 11, further comprising transmitting the message to the terminal apparatus or the vehicle.

13. The information processing method of claim 11, further comprising storing positional information for a plurality of healthcare professionals.

14. The information processing method of claim 13, further comprising transmitting the message to the healthcare professional whose positional information is close to a position of the patient.

* * * * *